United States Patent
Kakar

(10) Patent No.: US 8,579,630 B2
(45) Date of Patent: Nov. 12, 2013

(54) APPARATUS AND METHOD FOR MEASURING DENTIN HYPERSENSITIVITY

(76) Inventor: Ashish Kakar, New Delhi (IN)

( * ) Notice: Subject to any disclaimer, the term of this patent is extended or adjusted under 35 U.S.C. 154(b) by 0 days.

(21) Appl. No.: 13/389,857

(22) PCT Filed: Oct. 12, 2010

(86) PCT No.: PCT/IB2010/002604
§ 371 (c)(1),
(2), (4) Date: Mar. 13, 2012

(87) PCT Pub. No.: WO2011/018714
PCT Pub. Date: Feb. 17, 2011

(65) Prior Publication Data
US 2012/0202165 A1    Aug. 9, 2012

(51) Int. Cl.
*A61C 5/00*    (2006.01)

(52) U.S. Cl.
USPC .......................... 433/215; 433/27

(58) Field of Classification Search
USPC .......................... 433/27, 215, 229
See application file for complete search history.

(56) References Cited

U.S. PATENT DOCUMENTS

| | | | |
|---|---|---|---|
| 4,164,214 A * | 8/1979 | Stark et al. | 600/554 |
| 4,177,799 A * | 12/1979 | Masreliez | 600/554 |
| 4,485,823 A * | 12/1984 | Yamaguchi et al. | 600/552 |
| 4,680,825 A * | 7/1987 | White et al. | 15/105 |
| 4,841,987 A * | 6/1989 | Brown et al. | 600/590 |
| 4,960,132 A * | 10/1990 | Habekost | 600/589 |
| 5,040,539 A * | 8/1991 | Schmitt et al. | 600/340 |
| 5,518,008 A * | 5/1996 | Cucchiaro et al. | 600/590 |
| 5,536,245 A * | 7/1996 | Dahlbeck | 600/195 |
| 5,592,947 A * | 1/1997 | Lavigne et al. | 600/557 |
| 5,782,763 A * | 7/1998 | Bianco et al. | 600/407 |
| 5,874,066 A * | 2/1999 | Hack et al. | 424/49 |
| 5,879,312 A * | 3/1999 | Imoto | 600/587 |
| 5,897,510 A * | 4/1999 | Keller et al. | 600/594 |
| 5,904,658 A * | 5/1999 | Niederauer et al. | 600/587 |
| 6,413,220 B1 * | 7/2002 | Rose | 600/449 |
| 6,424,861 B2 * | 7/2002 | Meredith | 600/547 |
| 6,866,509 B2 * | 3/2005 | Jensen | 433/215 |
| 7,449,008 B2 * | 11/2008 | Hochman | 604/67 |
| 2007/0054243 A1 | 3/2007 | Schemmer et al. | |
| 2007/0167888 A1 | 7/2007 | Taylor | |
| 2007/0270727 A1 | 11/2007 | Khorassani Zadeh | |
| 2007/0276292 A1 * | 11/2007 | Hansma et al. | 600/587 |
| 2009/0056427 A1 * | 3/2009 | Hansma et al. | 73/82 |
| 2009/0093692 A1 * | 4/2009 | Hansma | 600/306 |
| 2010/0112512 A1 * | 5/2010 | Jones | 433/32 |
| 2011/0256496 A1 * | 10/2011 | Arzanpour | 433/27 |
| 2012/0053483 A1 * | 3/2012 | Doidge et al. | 600/544 |

* cited by examiner

*Primary Examiner* — Cris L Rodriguez
*Assistant Examiner* — Hao D Mai
(74) *Attorney, Agent, or Firm* — Lerner, David, Littenberg, Krumholz & Mentlik, LLP

(57) ABSTRACT

An apparatus for measuring dentin hypersensitivity is provided. The apparatus has a dental probe configured to apply force increasingly on a tooth until the applied force corresponds to a threshold force. Further, the apparatus has a load cell that is positioned in the dental probe. The load cell is configured to generate an electrical signal proportional to the applied force. Further, the apparatus has a microcontroller which is in communication with the load cell. The microcontroller is configured to determine an applied force value corresponding to the electrical signal. Furthermore, the apparatus has a display device. The display device is in communication with the microcontroller. The display device is configured to display the applied force value and a threshold force value digitally. The threshold force value is a quantifiable value of the applied force to which a patient responds and is a measure of the dentin hypersensitivity.

7 Claims, 3 Drawing Sheets

APPARATUS AND METHOD FOR MEASURING DENTIN HYPERSENSITIVITY

CROSS-REFERENCE TO RELATED PATENT APPLICATIONS

The present application is a national phase entry under 35 U.S.C. §371 of International Application No. PCT/IB2010/002604 filed Oct. 12, 2010, published in English, the disclosure of which is incorporated herein by reference.

FIELD OF THE INVENTION

The present invention relates generally to a dental diagnostic apparatus. More particularly, the present invention provides an apparatus for measuring dentin hypersensitivity and a method thereof.

BACKGROUND OF THE INVENTION

Dentin hypersensitivity is defined as painful response to external stimuli such as, tactile (feeling of pressure or pain upon touch), osmotic (sweet food/beverages), thermal (hot and cold food/beverages/air etc.), evaporative (air-movement) and/or chemical stimuli. It is well known that periodontal disease or receded gums cause dental sensitivity of teeth where a patient experiences pain or discomfort when his teeth are exposed to one or more of the external stimuli. The pain or discomfort is, typically, caused when dentin in the teeth gets exposed due to periodontal disease and/or receded gums. Dentin is a calcified tissue found in the inner part of teeth and forms the shape thereof and contains small pores or tubules which lead directly to intradental nerves of the teeth. The external stimuli to which the teeth are subjected can pass through the tubules and stimulate the teeth nerves causing pain and discomfort to a patient.

Conventionally, various methods and apparatuses exist for preventing and/or remedying dentin hypersensitivity of a patient. For example, several compositions are available for mineralizing/remineralizing/fluoridating/calcifying teeth to desensitize dentin. Further, methods and apparatuses exist for administering compositions to treat dental sensitivity. For example, existing apparatuses employ techniques involving electric current to administer iconic species like fluoride ions to treat dentin sensitivity. However, an efficient apparatus for measuring dentin sensitivity does not exist that would facilitate effective treatment of dentin sensitivity.

In light of the above, there is a need for a simple and effective apparatus and method for measuring dentin hypersensitivity. Further, there is a need for an apparatus and method that would provide an aid to evaluate effect of ongoing treatments for dentin hypersensitivity. In addition, there is a need for an apparatus and method which can quantify the degree of dentin hypersensitivity.

SUMMARY OF THE INVENTION

An apparatus for measuring dentin hypersensitivity is provided. The apparatus comprises a dental probe configured to apply force increasingly on a tooth until the applied force corresponds to a threshold force. The threshold force is a quantifiable value of the applied force to which a patient responds and is a measure of the dentin hypersensitivity. The apparatus further comprises a load cell that is positioned in the dental probe. The load cell is configured to generate an electrical signal proportional to the applied force. Further, the apparatus comprises a microcontroller which is in communication with the load cell. The microcontroller is configured to determine an applied force value corresponding to the electrical signal. Furthermore, the apparatus comprises a display device. The display device is in communication with the microcontroller. The display device is configured to display the applied force value and a threshold force value digitally.

In an embodiment of the present invention, a footswitch assembly is provided. The footswitch assembly is configured to facilitate a user to select one or more preset force values stored in the microcontroller. In another embodiment of the present invention, one or more buttons are provided. The one or more buttons are configured to facilitate a user to select one or more preset force values stored in the microcontroller. In yet another embodiment of the present invention, an alert device is provided. The alert device is configured to produce an audio alert when the applied force corresponds to one or more preset force values selected by a user. In these embodiments, switching to various preset force values facilitates gradual determination of the threshold force.

A method for measuring dentin hypersensitivity is provided. The method comprises the step of, firstly, selecting a preset force value from a set of preset force values. Switching to various preset force values facilitates gradual determination of a threshold force. Secondly, the method comprises the step of applying force on a tooth increasingly until the applied force corresponds to the threshold force. The force is applied using a dental probe having a load cell. Further, the method comprises reading the applied force value using a display device. The display device is connected to a microcontroller which converts electrical signal received from the load cell into applied force value. Furthermore, the method comprises the step of ascertaining a threshold force value digitally. The threshold force value is a quantifiable value of the applied force to which a patient responds and is a measure of the dentin hypersensitivity. Finally, the method comprises selecting another preset force value from the set of preset force values if the applied force does not correspond to the threshold force and repeating the abovementioned steps from applying force on the tooth till ascertaining threshold force value.

In an embodiment of the present invention, the preset force value is represented by any value between 1 and 9 with a multiplication factor. In another embodiment of the present invention, the method further comprises hearing an audio alert when the applied force corresponds to the preset force value and reading the preset force value displayed in a digital format using the display device. The audio alert is produced by an alert device which is connected to the microcontroller.

BRIEF DESCRIPTION OF THE ACCOMPANYING DRAWINGS

The present invention is described by way of embodiments illustrated in the accompanying drawings wherein.

DETAILED DESCRIPTION OF THE INVENTION

An apparatus and method for measuring tooth sensitivity is described herein. The invention provides for an apparatus and method that employs tactile stimulus for eliciting a response in a patient's teeth and monitoring the patient's response. The invention more specifically provides for an apparatus and method to determine dentin sensitivity of the patient at a particular probing force magnitude.

The following disclosure is provided in order to enable a person having ordinary skill in the art to practice the invention. Exemplary embodiments are provided only for illustrative purposes and various modifications will be readily apparent to persons skilled in the art. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

The present invention would now be discussed in context of embodiments as illustrated in the accompanying drawings.

Figure 1:
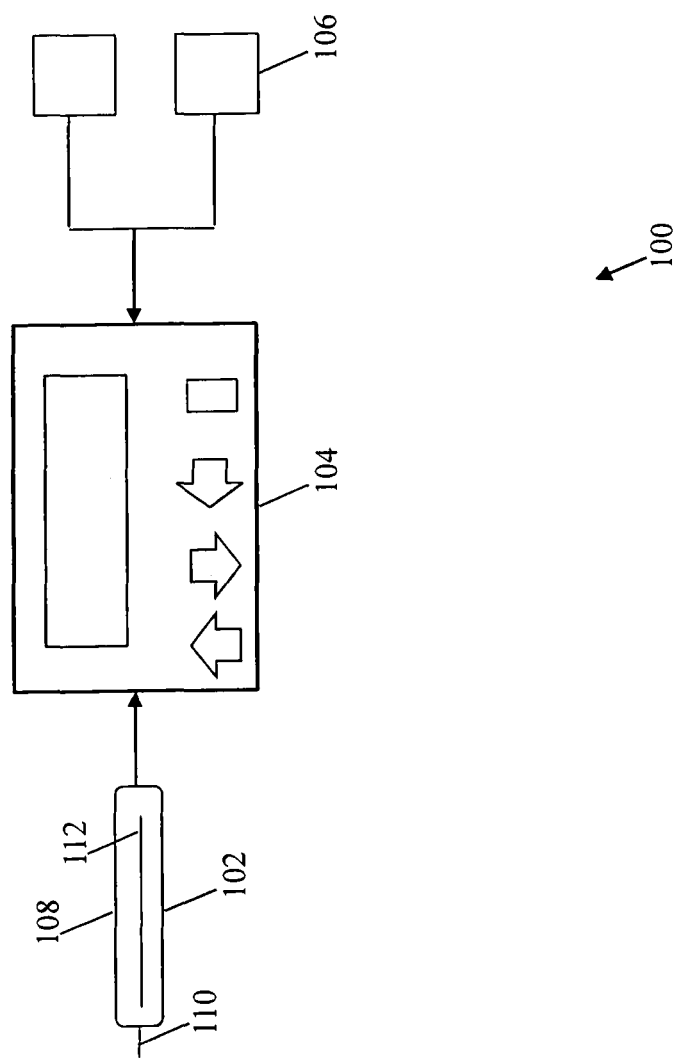
FIG. 1 is a block diagram illustrating an apparatus for measuring dentin sensitivity in accordance with an embodiment of the present invention.

FIG. 1 is a block diagram illustrating an apparatus 100 for measuring dentin sensitivity in accordance with an embodiment of the present invention. The apparatus 100 comprises a dental probe 102, a sensitivity measuring device 104, and a foot switch assembly 106. The dental probe 102 further comprises a probe body 108, a probe tip 110, and a load cell 112.

Dental probe 102 is a handheld instrument which may be used by a practitioner, e.g. dentist, to examine or evaluate teeth of a patient. In an embodiment of the present invention, the dental probe 102 may be electrically coupled to the sensitivity measuring device 104 using suitable wire/cables. The dental probe 102 may be adapted to sense tactile stimulus and transmit a proportional output electrical signal to the sensitivity measuring device 104.

Sensitivity measuring device 104 is an electronic device which is used to measure dentin hypersensitivity. In various embodiments of the present invention, the sensitivity measuring device 104 is a specialized processing device which may be electrically coupled to the dental probe 102. The sensitivity measuring device 104 may be employed to perform operations such as receiving the electrical signal from the dental probe 102 and processing the electrical signal. Further, the sensitivity measuring device 104 may be employed to display information obtained as a result of processing the electrical signal to facilitate measurement of sensitivity of a tooth of a patient. In an embodiment of the present invention, the sensitivity measuring device 104 may be provided with buttons which can be operated manually. The buttons are adapted to trigger functionalities relating to operation of the sensitivity measuring device 104.

In another embodiment of the present invention, the sensitivity measuring device 104 may be operated using wireless connectivity. For example, the sensitivity measuring device 104 may be operated by employing a Personal Digital Assistant (PDA) which is a handheld device that may be used for remote operation of the sensitivity measuring device 104. The PDA may be provided with software capable of triggering functionalities relating to the operation of the sensitivity measuring device 104 over a wireless link. The wireless link employed by the PDA for communicating with the sensitivity measuring device 104 may be bluetooth wireless connectivity, Wireless Fidelity (WiFi)/WLAN/IEEE 802.11 connectivity, infrared connectivity etc.

In another embodiment of the present invention, the sensitivity measuring device 104 may be operated by employing the foot switch assembly 106. Foot switch assembly 106 is a device which may be used by a practitioner, e.g. dentist, to trigger functionalities relating to the operation of the sensitivity measuring device 104. In an embodiment of the present invention, the foot switch assembly 106 is connected to the sensitivity measuring device 104 using any known electrical cable, e.g. RS232 cable. The foot switch assembly 106 comprises two foot switches, namely up and down foot switches. In an embodiment of the present invention, the foot switches may be Single Pole Single Throw (SPST) switch that are on-off switches and consumes power when depressed. SPST are normally open contacts and when the switch is depressed, the normally open contacts are closed and electrical signal is transmitted via the electrical cable to the sensitivity measuring device 104. In various embodiments of the present invention, the foot switch assembly 106 is used to activate various operating modes of the apparatus 100 for facilitating measurement of force applied on the dental probe 102. In an embodiment of the present invention, the force may be applied on the probe body 108 of the dental probe 102 by the practitioner.

The probe body 108 permits the practitioner to manoeuvre the dental probe 102 for dental examination. In various embodiments of the present invention, the probe body 108 provides support to the dental probe 102 and permits the practitioner to engage the dental probe 102 with the exposed dentin of a patient. The probe body 108 may be mechanically coupled to the probe tip 110 by any conventional arrangement.

The probe tip 110 may be an elongated and a blunt needle which may be used to engage with the dentin of a patient. In various embodiments of the present invention, the probe tip 110 may be in any conventional mechanical arrangement with the probe body 108. The probe tip 110 may be made of stainless steel, metal or plastic and is disposable. Alternatively, the probe tip 110 may be fastened to the dental probe 102 and sterilized after every use. Additionally, a thin transparent cover may be used with the probe tip 110 to maintain the sterilization. In various embodiments of the present invention, during periodontal examination, the probe tip 110 is inserted into mouth of a patient to engage with the dentin. Force is applied on the dentin by gripping the probe body 108 and pressing the probe tip 110 against the dentin. The applied force may be sensed by the load cell 112 which is disposed in the dental probe 102.

Load cell 112 is an electronic device that converts force into an electrical signal and may be used for sensing force. The electrical signal output may be typically in the order of a few millivolts. In various embodiments of the present invention, the load cell 112 may reside in the interior of the distal end of the probe body 108. The load cell 112 may comprise a strain gauge (not shown) which may be attached to the load cell 112 by any conventional mechanical arrangement. The strain gauge is made of conductive material that gets deformed with the application of force and converts the deformation into an electrical signal. In an embodiment of the present invention, the strain gauge may employ a known wheatstone bridge circuit. A wheatstone bridge circuit is a divided bridge circuit which is used for the measurement of static or dynamic electrical resistance. In an embodiment of the present invention, the strain gauge may be a semiconductor strain gauge. In another embodiment of the present invention, the strain gauge may be a foil strain gauge. In yet another embodiment of the present invention, the strain gauge may be a bonded semiconductor or a bonded foil strain gauge. In yet another embodiment of the present invention, the load cell 112 may be a beam load cell capable of measuring low bending forces. Further, the load cell 112 may be a beam load cell having miniature dimensions. The miniature dimensions of the load cell 112 allow the load cell 112 to easily integrate into the dental probe 102. In an embodiment of the present invention, when a force is applied on the probe body 108, electrical resistance of the strain gauge in the load cell 112 changes in proportion to the force resulting in an output electrical signal. The output electrical signal is transmitted to the sensitivity measuring device 104 for facilitating measurement of tooth sensitivity.

Figure 2:
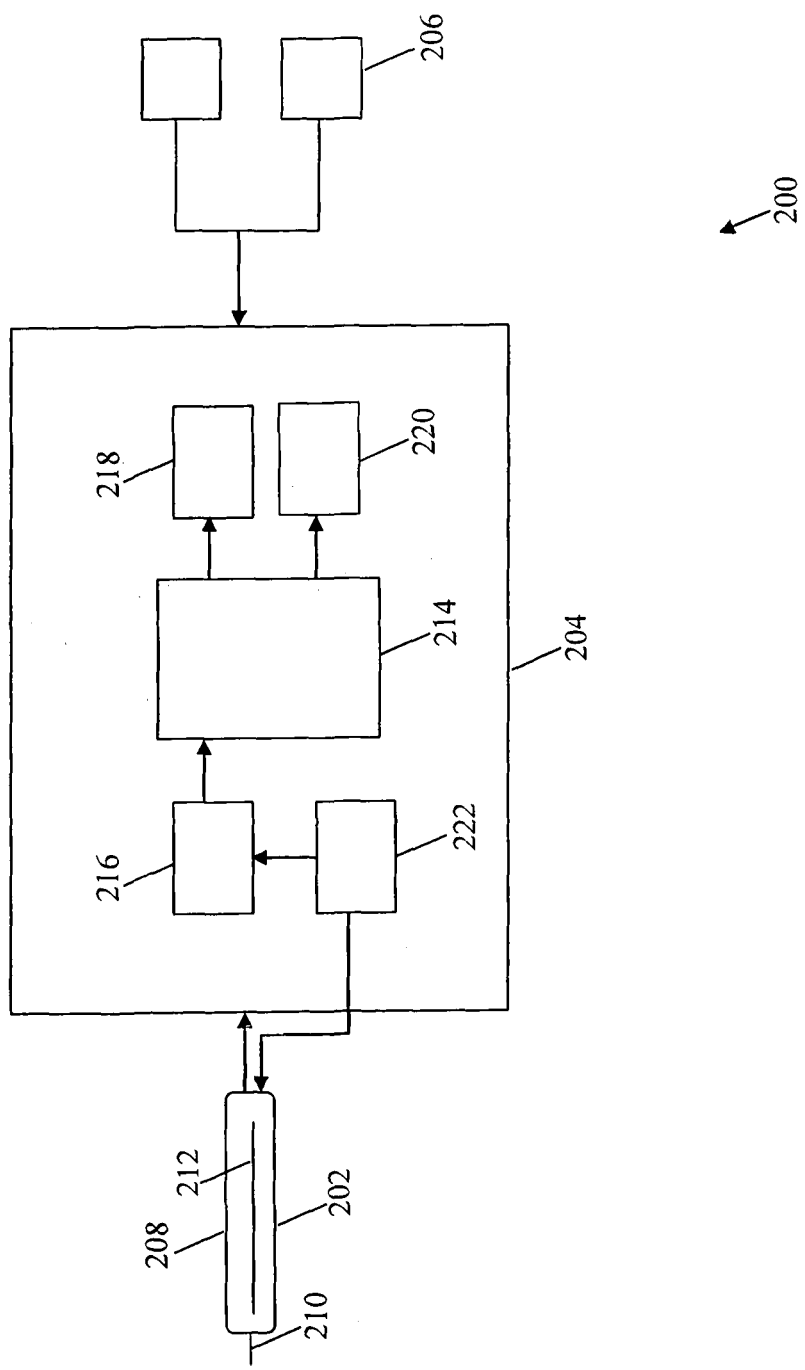
FIG. 2 illustrates a detailed block diagram of a sensitivity measuring device for measuring dentin sensitivity in accordance with an embodiment of the present invention.

FIG. 2 is a detailed block diagram 200 of the sensitivity measuring device 204 for measuring dental sensitivity in accordance with an embodiment of the present invention. The sensitivity measuring device 204 comprises a microcontroller 214, an Analog to Digital Converter (ADC) 216, a display device 218, an alert device 220, and a Switched Mode Power Supply (SMPS) 222.

Microcontroller 214 is an electronic integrated circuit that comprises a memory (not shown), a processor (not shown) and input/output ports (not shown) for interfacing with peripheral devices. In an embodiment of the present invention, the microcontroller 214 may be AT Mega 88. AT Mega 88 is a low power Complementary Metal Oxide Semiconductor (CMOS) 8-bit microcontroller based on Reduced Instruction Set Computer (RISC) architecture which operates at high speed and with optimal power consumption. In another embodiment of the present invention, the microcontroller 214 may be any other microcontroller suitable for interconnection with the dental probe 202.

In yet another embodiment of the present invention, the electrical signal output from the load cell 212 is received by the microcontroller 214 via suitable input/output ports. In yet another embodiment of the present invention, the microcontroller 214 receives the electrical signal output of the load cell 212 from the ADC 216 via suitable input/output ports. The magnitude of the electrical signal received by the microcontroller 214 is proportional to the magnitude of force applied on the probe body 208 which is mechanically connected to the probe tip 210 that is pressed against the dentin by the practitioner. The microcontroller 214 comprises a converting means, which may be a software module, for converting the electrical signal into a force value. Subsequently, the microcontroller 214 enables display of the force value in the display device 218 to facilitate the practitioner to estimate the applied force.

In an embodiment of the present invention, the microcontroller 214 is initialized using a reset pin provided on the microcontroller chip. In another embodiment of the present invention, current data in the microcontroller 214 may be stored and saved in a non volatile Random Access Memory (RAM) when Direct Current (DC) voltage is less than 4.7V and the microcontroller 214 is on the verge of shutting off. In yet another embodiment of the present invention, the microcontroller 214 is provided with an auxiliary supply to protect the microcontroller 214 from unwanted signals and noises.

ADC 216 is an electronic integrated circuit which converts an analog signal to a digital signal. In various embodiments of the present invention, the ADC 216 may be in communication with the load cell 212 and the microcontroller 214. The ADC 216 operates conventionally to sense analog voltage signal output from the load cell 212, convert the analog voltage signal into digital data and provide the digital data to the microcontroller 214 via the suitable input/output ports. In an embodiment of the present invention, the ADC 216 may be an AD7705/AD7706 or any other analog to digital converter capable of receiving low level input signals directly from the load cell 212 and producing a digital signal output. The digital signal output is read and scaled by the microcontroller 214 for processing the signal and facilitating display of the measured force in the display device 218.

Display device 218 is a device which may be used for presenting information digitally. In various embodiments of the present invention, input/output ports of the microcontroller 214 channelize flow of data between the microcontroller 214 and the display device 218. In an embodiment of the present invention, the display device 218 may comprise a Liquid Crystal Device (LCD) display and facilitates digital display of measurements in 'grams'. In yet another embodiment of the present invention, the display device 218 is a Common Cathode (CC) display. The display may be a 3-digit 7-segment and a dot point display. In an embodiment of the present invention, the force value obtained in the microcontroller 214 is transmitted to the display device 218 which is displayed in grams, thus, facilitating a digital visual read out of the force applied on the dental probe 202. In another embodiment of the present invention, the force value may also be presented in an analog format.

In various embodiments of the present invention, the display device 218 may be further provided with a front panel that comprises buttons. The buttons can be operated manually by a practitioner e.g. dentist to operate in certain operating modes e.g. limit mode and calibration mode. Calibration mode is to facilitate accuracy of the display device 218 and limit mode is to enable generation of an alert by the alert device 220 under certain predetermined conditions. The predetermined conditions are conditions subject to which the amount of force applied on a patient's tooth may be controlled in order to prevent damage to the tooth. For example, the predetermined conditions may be based on the or patient's age group, patients past tooth sensitivity measurement record, etc.

In an embodiment of the present invention, up and down arrows buttons (as depicted in FIG. 1) may be provided in the front panel of the display device 218. The up and down arrow buttons may be used to increase or decrease values displayed in the display device 218 in the calibration mode as well as the limit mode. The limit mode allows the practitioner to select a range of force for triggering the alert device 220 based on certain predetermined conditions as discussed above.

Alert device 220 is a transducer that converts electrical energy into sound. In various embodiments of the present invention, the alert device 220 may be a beeper that is driven by the microcontroller 214 to produce a beep sound under certain predetermined conditions. In various embodiments of the present invention, the alert device 220 produces a beep sound when the force applied on the probe body 208 is between a lower limit and an upper limit of values stored in the microcontroller's 214 memory. The beep sound, thus, indicates that the force applied is approaching the upper limit of the stored values. In an embodiment of the present invention, the microcontroller 214 drives the alert device 220 to produce a continuous sound when the force applied exceeds the upper limit of the values. In another embodiment of the present invention, the alert device 220 produces the beep sound and the continuous beep sound when the microcontroller's 214 output port connected to the alert device 220 oscillates at a frequency of 0.5 Hz.

In an embodiment of the present invention, values from 1 to 9 may be preset in the microcontroller's 214 memory. The values represent preset force values with a multiplication factor. The lower limits are configured to be in terms of 8's factor and the upper limits are configured to be in terms of 10's factor in all the 9 values. For example, if value 3 is selected by the practitioner, the lower limit shall correspond to "24" and upper limit shall correspond to "30". Beep sound will generate when the applied force lies between 24 grams and 30 grams and a continuous sound will be produced when the applied force reaches 30 grams. In yet another embodiment of the present invention, a continuous beep sound may be generated when the applied force exceeds 30 grams. In an embodiment of the present invention, the values may be selected by the practitioner by operating the arrow buttons. In yet another embodiment of the present invention, the values are programmed for a range of −10% for all presets.

In another embodiment of the present invention, the values may be selected by operating the foot switch assembly 206. The foot switch assembly 206 comprises up and down switches. In an embodiment of the present invention, in the limit mode, the foot switches may be operated by the practitioner to select preset force values in the microcontroller 214 by selecting any value between 1 and 9. In particular, values can be increased and decreased by depressing the up and down foot switches respectively. The electrical signals generated as a result of depressing the up and down switches are transmitted to the microcontroller 214. The electrical signals are read by the microcontroller 214 and a preset force value is selected. If both the up and down foot switches are depressed at the same time, the input electrical signal from the foot switch assembly 206 informs the microcontroller 214 that both the up and down foot switches have been depressed concurrently. Subsequently, the microcontroller 214 resets the display device 218 and "00" is displayed on the display device 218.

In various embodiments of the present invention, in the calibration mode, the display device 218 may be adjusted to full scale. Full scale is the maximum value up to which readings of measured force may be displayed. In an embodiment of the present invention, the maximum value is preset in the microcontroller 214. If force applied exceeds the maximum value, the display will show error. In yet another embodiment of the present invention, the display is adjusted to least count so that the smallest value can also be measured. For example, if 0002 is fed in the microcontroller 214 as least count, then readings of measured force will be displayed as 2, 4, 6, 8, 10 in terms of 2's factor and if it is 0001, the readings will be displayed as 1, 2, 3, 4.

In yet another embodiment of the present invention, calibration of the load cell 212 may be checked. In this embodiment, value of a known weight is fed into the microcontroller 214 using the up and down arrow buttons. An Acknowledgment (ACK) button (not shown) provided in the panel of the display device 218 is pressed to display the fed value. Subsequently, the known weight is loaded onto the load cell 212. The value of the loaded known weight as displayed by the display device 218 is compared with the value that is fed. If there is a match, the load cell 212 is said to be calibrated and if there is no match, the load cell 212 needs to be calibrated again. Calibration techniques known in the art may be employed to calibrate the load cell 212 for accurate measurement of the applied force.

Switched Mode Power Supply (SMPS) 222 is an electronic power supply unit that incorporates a switching regulator in order to provide required Direct Current (DC) voltage to the dental probe 202 and the sensitivity measuring device 204. In various embodiments of the present invention, the SMPS 222 provides a 5V supply to components in the sensitivity measuring device 204. For example, the SMPS 222 provides a 5V/1A supply to the ADC (216). Further, the SMPS 222 provides 12V/200 mA power supply to the load cell 212 in the dental probe 202. The SMPS 222 is coupled to an input Alternating Current (AC) voltage source which may provide an input AC voltage between low line and high line values (e.g. between 85 VAC and 260 VAC).

Operationally, in various embodiments of the present invention, force applied by the practitioner on tooth of a patient is measured and displayed in the display device in a digital format. The force at which the patient expresses discomfort or pain is recorded as a measure of sensitivity of tooth of a patient. Hence, tooth/dentin sensitivity can be quantified. A menu driven program may also be invoked by the practitioner to facilitate entry of patient information, such as name, address etc. for maintaining the patient's record. The record containing the patient information and the tooth sensitivity measurement data may be printed on a paper or displayed on the display device 218. This measurement may be used as a reference for testing the effect of treatment for dental sensitivity provided to the patient at a later stage.

Figure 3:
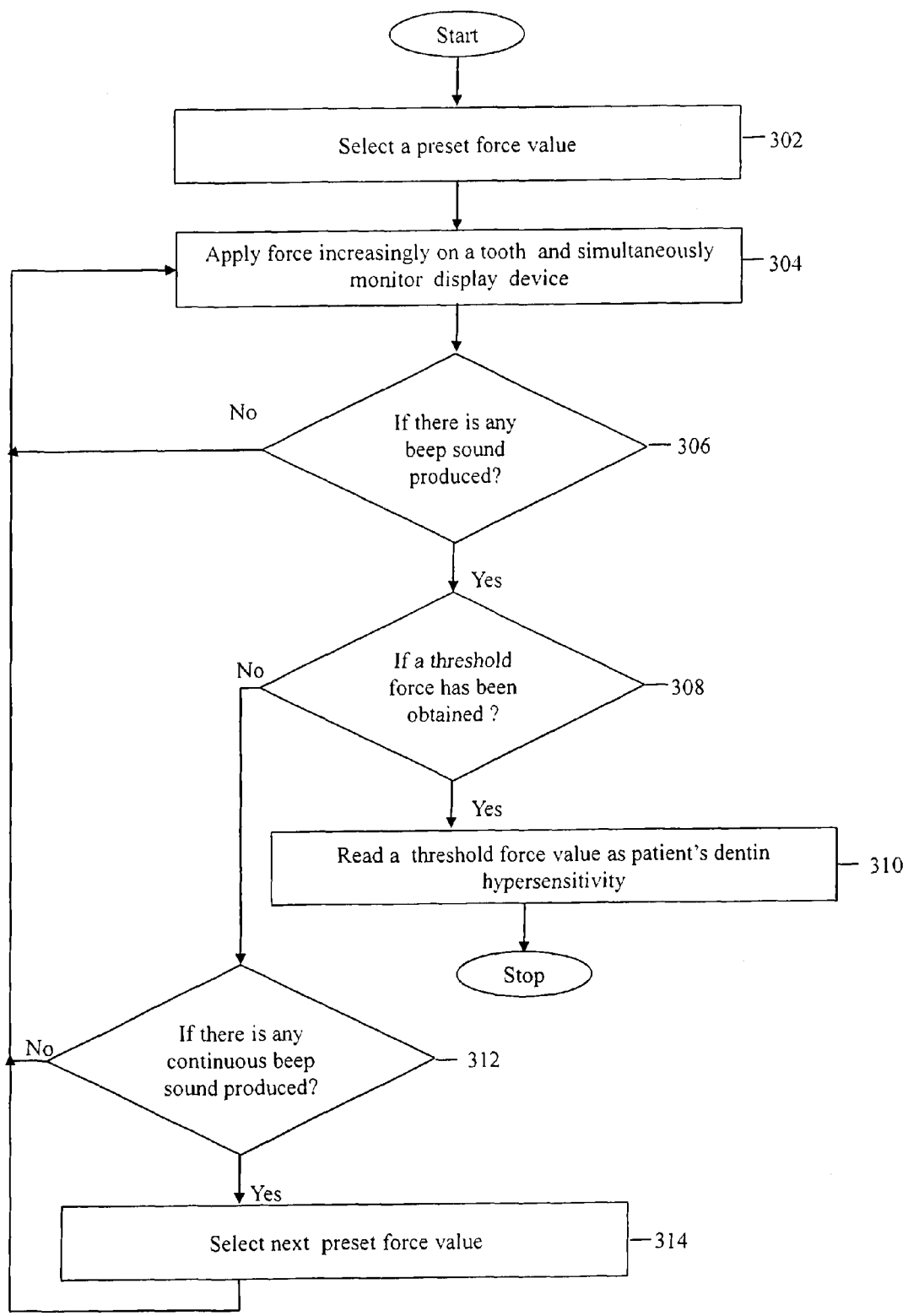
FIG. 3 is a flowchart illustrating a method for measuring dentin sensitivity in accordance with an embodiment of the present invention.

FIG. 3 is a flowchart illustrating a method for measuring dental sensitivity in accordance with an embodiment of the present invention.

At step 302, a preset force value is selected from a set of preset force values. In various embodiments of the present invention, a preset force value may be selected by a practitioner e.g. a dentist based on certain criteria. For example, the criteria may be patient's age group, an initial examination of patient's tooth, patients past tooth sensitivity measurement record, etc. The basis of such criteria is to ensure that the force applied on a patient's tooth does not cause any damage to the tooth.

In various embodiments of the present invention, preset force values are represented by values from 1 to 9 with a multiplication factor and are stored in a microcontroller's memory. For example, lower limit of each value is configured to be in terms of 8's factor and the upper limit of each value is configured to be in terms of 10's factor in all the 9 values. Thus, for values from 1 to 9, the upper limit settings are 10, 20, 30, 40, 50, 60, 70, 80, 90 and the lower limit settings are 8, 16, 24, 32, 40, 48, 56, 64, 72 grams respectively. The lower limit settings are 20% lower than the upper limit settings.

At step 304, increasing force is applied on a tooth and simultaneous monitoring of the display device is performed. In an embodiment of the present invention, force is applied by a practitioner, e.g. a dentist on the tooth of a patient using a dental probe for measuring sensitivity of the tooth. The practitioner positions the dental probe appropriately on the tooth of the patient and applies force on the tooth by gripping a probe body of the dental probe and exerting force on the probe body by hand. Subsequently, the practitioner gradually increases the magnitude of force applied on the tooth.

In another embodiment of the present invention, the dental probe comprises a load cell which senses the applied force and generates an output electrical signal proportional to the applied force. For example, the electrical signal may be a voltage signal with amplitude proportional to the magnitude of the applied force. The microcontroller receives the electrical signal from the load cell and converts the electrical signal into the applied force value. For example, software module in the microcontroller may obtain the applied force value from amplitude of output voltage signal. Subsequently, the applied force value is displayed using a digital display device which facilitates the practitioner to read the applied force.

At step 306, a check is, performed to determine if there is any beep sound. In various embodiments of the present invention, a beep sound is produced when the applied force reaches the lower limit and is close to the upper limit of the selected preset force value. For example, if value '4' is selected by the practitioner, a broken beep sound may be produced when the applied force lies between 32 grams and 40 grams. The broken beep sound generated when the applied force lies between 32 grams and 40 grams indicates that the applied force is approaching 40 grams. When the applied force crosses 40 grams, a continuous beep is generated.

If the beep sound has been produced, then, at step 308, a check is performed to determine whether a threshold force has been obtained. In various embodiments of the present invention, force is applied on the tooth till the applied force corresponds to a threshold force. Threshold force is the force at which the patient experiences pain for the first time.

If the threshold force has been obtained, then, at step 310, a threshold force value is determined from the display device. In various embodiments of the present invention, if the applied force corresponds to the threshold force, no more force is applied by the practitioner on the patient's tooth. The threshold force value is then read by the practitioner from the display device and is recorded as dentin hypersensitivity of the patient.

If the threshold force has not been obtained, then, at step 312, a check is performed to determine if a continuous beep sound has been produced. In various embodiments of the present invention, a continuous beep sound is produced when the applied force reaches and exceeds the upper limit. For example, if value '4' is selected, a continuous sound is produced when the applied force exceeds 40 grams. In this example, upper limit corresponds to 40 grams. If the continuous beep sound has been produced, then at step 314, another preset force value is selected and steps 304 to 314 are repeated. Thus, by switching to various preset force values the threshold force can be gradually determined.

If the threshold force has not been obtained and the continuous beep sound has not been produced, steps 304 to 314 are repeated for the same preset force value selected at step 302.

The present invention may be implemented in numerous ways including as a apparatus, method, or a computer program product such as a computer readable storage medium or a computer network wherein programming instructions are communicated from a remote location.

While the exemplary embodiments of the present invention are described and illustrated herein, it will be appreciated that they are merely illustrative. It will be understood by those skilled in the art that various changes in form and detail may be made therein without departing from or offending the spirit and scope of the invention.

The invention claimed is:

1. An apparatus for measuring dentin hypersensitivity, the apparatus comprising:
   a dental probe configured to apply force increasingly on a tooth until the applied force corresponds to a threshold force;
   a load cell, positioned in the dental probe, configured to generate an electrical signal proportional to the applied force;
   a microcontroller configured to:
   determine one or more selected preset values from a set of preset values, wherein the selection of one or more preset values is carried out for gradual determination of the threshold force;
   determine that the applied force has reached the threshold force for a particular selected preset value, wherein the applied force is detected based on the electrical signal received from the load cell; and
   ascertain an applied force value corresponding to the applied force and a threshold force value corresponding to the threshold force, wherein the threshold force value is a quantifiable value of the applied force to which a patient responds and is a measure of the dentin hypersensitivity; and
   a display device, in communication with the microcontroller, configured to display the applied force value and the threshold force value digitally.

2. The apparatus of claim 1 further comprising:
   a footswitch assembly configured to facilitate a user to select one or more preset force values stored in the microcontroller.

3. The apparatus of claim 1 further comprising:
   one or more buttons configured to facilitate a user to select one or more preset force values stored in the microcontroller.

4. The apparatus of claim 1 further comprising:
   an alert device configured to produce an audio alert when the applied force corresponds to one or more preset force values selected by a user.

5. A method for measuring dentin hypersensitivity, the method comprising the steps of:
   (i) selecting a preset force value from a set of preset force values, wherein switching to various preset force values facilitates gradual determination of a threshold force;
   (ii) applying force on a tooth increasingly, using a dental probe having a load cell, until the applied force corresponds to the threshold force;
   (iii) reading the applied force value using a display device connected to a microcontroller which converts electrical signal received from the load cell into applied force value;
   (iv) ascertaining a threshold force value digitally, wherein the threshold force value is a quantifiable value of the applied force to which a patient responds and is a measure of the dentin hypersensitivity; and
   (v) repeating the steps (ii) to (iv) after selecting another preset force value from the set of preset force values if the applied force does not correspond to the threshold force.

6. The method of claim 5, wherein the preset force value is represented by any value between 1 and 9 with a multiplication factor.

7. The method of claim 5 further comprising:
   hearing an audio alert, produced by an alert device connected to the microcontroller, when the applied force corresponds to the preset force value; and
   reading the preset force value displayed in a digital format using the display device.

* * * * *